US010280189B2

(12) United States Patent
Burck et al.

(10) Patent No.: US 10,280,189 B2
(45) Date of Patent: May 7, 2019

(54) METHOD FOR THE SYNTHESIS OF AMINOALKYLENEPHOSPHONIC ACID

(71) Applicant: MONSANTO TECHNOLOGY LLC, St. Louis, MO (US)

(72) Inventors: Sebastian Burck, Louvain-la-Neuve (BE); Cedric Nicolas Leclercq, Limal (BE); Patrick Notte, Wavre (BE)

(73) Assignee: Monsanto Technology LLC, St. Louis, MO (US)

( * ) Notice: Subject to any disclaimer, the term of this patent is extended or adjusted under 35 U.S.C. 154(b) by 245 days.

(21) Appl. No.: 14/415,686

(22) PCT Filed: Jul. 17, 2013

(86) PCT No.: PCT/EP2013/065121
§ 371 (c)(1),
(2) Date: Jan. 19, 2015

(87) PCT Pub. No.: WO2014/012987
PCT Pub. Date: Jan. 23, 2014

(65) Prior Publication Data
US 2015/0225431 A1 Aug. 13, 2015

(30) Foreign Application Priority Data
Jul. 17, 2012 (EP) .................................... 12176753

(51) Int. Cl.
*C07F 9/653* (2006.01)
*C07F 9/6533* (2006.01)
*C07F 9/572* (2006.01)
*C07F 9/6506* (2006.01)
*C07F 9/38* (2006.01)

(52) U.S. Cl.
CPC .......... *C07F 9/6533* (2013.01); *C07F 9/3808* (2013.01); *C07F 9/3813* (2013.01); *C07F 9/3873* (2013.01); *C07F 9/572* (2013.01); *C07F 9/5728* (2013.01); *C07F 9/653* (2013.01); *C07F 9/6506* (2013.01)

(58) Field of Classification Search
CPC .................................................... C07F 9/6533
See application file for complete search history.

(56) References Cited

U.S. PATENT DOCUMENTS

| | | | |
|---|---|---|---|
| 3,288,846 A | 11/1966 | Irani et al. | |
| 3,451,937 A | 6/1969 | Quimby | |
| 3,455,675 A | 7/1969 | Irani et al. | |
| 3,796,749 A | 3/1974 | Krueger et al. | |
| 3,799,758 A | 3/1974 | Franz et al. | |
| 3,816,517 A | 6/1974 | Krueger et al. | |
| 3,832,393 A | 8/1974 | Krueger et al. | |
| 3,927,080 A | 12/1975 | Gaertner | |
| 3,969,398 A | 7/1976 | Hershman | |
| 4,065,491 A | 12/1977 | Pfliegel et al. | |
| 4,211,547 A | 7/1980 | Gaertner | |
| 4,237,065 A | 12/1980 | Ehrat | |
| 4,400,330 A | 8/1983 | Wong et al. | |
| 4,407,761 A | 10/1983 | Blum et al. | |
| 4,422,982 A | 12/1983 | Subramanian | |
| 4,617,415 A | 10/1986 | Balthazor et al. | |
| 4,624,937 A | 11/1986 | Chou | |
| 4,654,429 A | 3/1987 | Balthazor et al. | |
| 4,657,705 A | 4/1987 | Miller et al. | |
| 4,804,499 A | 2/1989 | Miller et al. | |
| 4,931,585 A | 6/1990 | Pelyva et al. | |
| 5,155,257 A | 10/1992 | Kleiner | |
| 5,312,972 A | 5/1994 | Cullen | |
| 5,312,973 A | 5/1994 | Donadello | |
| 5,688,994 A | 11/1997 | Baysdon et al. | |
| 7,084,298 B2 | 8/2006 | Maase et al. | |
| 9,150,599 B2 | 10/2015 | Burck et al. | |
| 2004/0024180 A1 | 2/2004 | Drauz et al. | |
| 2011/0118502 A1 | 5/2011 | Notte et al. | |
| 2015/0166584 A1 | 6/2015 | Devaux et al. | |
| 2015/0232493 A1 | 8/2015 | Notte et al. | |

FOREIGN PATENT DOCUMENTS

| | | |
|---|---|---|
| CA | 1039739 | 10/1978 |
| CH | 275435 | 5/1951 |
| CH | 620223 | 11/1980 |
| CN | 1631894 | 6/2005 |
| CN | 1285600 | 11/2006 |
| DE | 3903715 | 8/1989 |
| DE | 3903716 | 8/1989 |
| DE | 4026026 | 2/1992 |
| DE | 19909200 | 3/2000 |
| DE | 19914375 | 10/2000 |
| EP | 0480307 | 4/1992 |
| EP | 0537786 | 4/1993 |
| EP | 0595598 | 5/1994 |
| EP | 0638577 | 2/1995 |
| EP | 1681294 | 7/2006 |
| EP | 1681295 | 7/2006 |
| EP | 1932850 A1 | 6/2008 |
| EP | 2112156 | 10/2009 |
| ES | 2018746 | 5/1991 |
| GB | 1142294 | 2/1969 |
| GB | 1230121 | 4/1971 |
| GB | 2154588 | 9/1985 |
| GB | 2154589 | 9/1985 |

(Continued)

OTHER PUBLICATIONS

International Search Report for PCT/EP2013/065121, Completed by the European Patent Office on Sep. 11, 2013, 3 pages.

(Continued)

*Primary Examiner* — Shawquia Jackson
(74) *Attorney, Agent, or Firm* — Stinson Leonard Street LLP; Erin C. Robert

(57) ABSTRACT

A method for the synthesis of an aminoalkylenephosphonic acid or its phosphonate esters including the following steps: a) forming, in the presence of an aldehyde or ketone and an acid catalyst, a reaction mixture by mixing a compound having at least one $HNR^1R^2$ moiety or a salt thereof, with a compound having one or more P—O—P anhydride moieties, the moieties having one P atom at the oxidation state (+III) and one P atom at the oxidation state (+III) or (+V), wherein the ratio of moles of aldehyde or ketone to N—H moieties is 1 or more and wherein the ratio of N—H moieties to P—O—P anhydride moieties is 0.3 or more, and b) recovering the resulting aminoalkylenephosphonic acid having compound or its phosphonate esters.

26 Claims, No Drawings

(56) References Cited

FOREIGN PATENT DOCUMENTS

| | | |
|---|---|---|
| JP | 5775990 | 5/1982 |
| JP | 2007022956 | 2/2007 |
| RO | 101476 | 12/1991 |
| RU | 2402558 C2 | 10/2010 |
| WO | 9415939 | 7/1994 |
| WO | 9422880 | 10/1994 |
| WO | 9640698 | 12/1996 |
| WO | 9819992 | 5/1998 |
| WO | 9835930 | 8/1998 |
| WO | 0002888 | 1/2000 |
| WO | 0009520 | 2/2000 |
| WO | 0014093 | 3/2000 |
| WO | 0192208 | 12/2001 |
| WO | 02055527 | 7/2002 |
| WO | 2006074729 A1 | 7/2006 |
| WO | 2006107824 | 10/2006 |
| WO | 2009068636 | 6/2009 |
| WO | 2009130322 | 10/2009 |
| WO | 2010055056 | 5/2010 |
| WO | 2010136566 A1 | 12/2010 |
| WO | 2010136574 | 12/2010 |
| WO | 2011039378 | 4/2011 |
| WO | 2011051309 | 5/2011 |

OTHER PUBLICATIONS

European Search Report for European Application No. 12176753, Completed by the European Patent Office on Jan. 9, 2013, 5 pages.

Arizpe et al. Eur. J. Org. Chem. 2011, p. 3074-3081, "Stereodivergent synthesis of two a-aminophosphonic acids characterized by a cis-fused octahydroindole system."

Tapia-Benavidis et al. Heterocycles 1997, vol. 45, p. 1679-1686, "Syntheses of N-Substituted 2,5-Piperazindiones."

Merck Index, entry for nitrilotriacetic acid, downloaded on Jun. 10, 2017, Last revised in 2013, 2 Pages, https://www.rce.org/MerckIndex/monograph/m7935/nitrilotriacetic%/20acid?q=authorize.

Greenwood et al. Chemistry of the Elements, 2nd ed., Chapter 123.5, p. 503-510, 1998, "Phosphorus Oxides, Sulfides, Selenides and Related compounds".

Boroujeni, Synthesis and Reactivity in Inorganic, Matal-Organic, and Nano-Metal Chemisty 2011, vol. 41, pp. 173-176, "Synthesis of a-Aminophosphonates Using Polystyrene Supported Al(Otf)3 as a Heterogeneous Catalyst".

Corbridge, Phosphorus Chemistry, Biochemistry, and Technology, 6th Edition, D.E.C. Corbridge, Ed, 2013, Uploaded in 2 Parts, All together 118 Pages, "A Phosphides of Non-Metals".

Natchev, Ivan, "N α,N ω-Diphosphono-, Diphosphino-Methyl-L-α,ω-Diaminocarboxylic Acids," Phosphorus and Sulfur and the Related Elements, 1988, vol. 37, pp. 143-148.

Zecchini et al., "A convenient route to pyrrolidine-2-phosphonic acid dipeptides," International Journal of Peptide and Protein Research, 1989, vol. 34, pp. 33-36.

Van Der Veken et al., "Irreversible Inhibition of Dipeptidyl Peptidase 8 by Dipeptide-Derived Diaryl Phosphonates," J. Med. Chem., 2007, vol. 50, pp. 5568-5570.

Petersen et al., "α-Ureidoalkylierung von Phosphor(III)-Verbindungen," Liebigs Ann. Chem., 1972, vol. 766, pp. 58-72.

METHOD FOR THE SYNTHESIS OF AMINOALKYLENEPHOSPHONIC ACID

CROSS-REFERENCE TO RELATED APPLICATION

This application is the U.S. national phase of PCT Application No. PCT/EP2013/065121 filed on Jul. 17, 2013, which claims priority to EP Patent Application No. 12176753.7 filed on Jul. 17, 2012, the disclosures of which are incorporated in their entirety by reference herein.

FIELD OF THE INVENTION

The present invention is related to a method for the synthesis of compounds comprising aminoalkylenephosphonic acid moieties or their phosphonate esters.

STATE OF THE ART

Aminoalkylenephosphonic acid compounds are well known in the art and have found widespread commercial acceptance for a variety of applications including phytotoxicant, water-treatment, scale-inhibition, detergent additives, sequestrants, marine-oil drilling adjuvants and as pharmaceutical components. It is well known that such applications preferably require aminoalkylenephosphonic acids wherein a majority of the nitrogen substituents are alkylenephosphonic acid groups.

EP 0595598 patent discloses a process for preparing N-(phosphonomethyl)iminodiacetic acid wherein solutions of an alkali metal salt of iminodiacetic acid are reacted with formaldehyde so as to form the alkali metal salt of hydroxymethyliminodiacetic acid which subsequently can be reacted with a phosphorous source such as phosphorous acid to produce N-phosphonomethyl iminodiacetic acid in good yield.

RO101476 patent discloses a method for the manufacture of dialkyl-N,N,-bis-(2-hydroxyethyl)-aminomethylphosphonate from diethylamine, paraformaldehyde and dialkyl phosphite as a 23-24% weight solution in toluene in the presence of glacial-acetic acid catalyst.

WO 94/22880 patent application discloses a process for the manufacture of aminomethanephosphonic acid comprising: a) reacting a compound of formula: R—$CH_2$—NH—CO—NH—$CH_2$—R' wherein R and R', represents a halogen, hydroxyl, $C_1$-$C_4$ alkoxy, aryloxy and $C_1$-$C_4$ alkylester groups, with a phosphonating agent, selected from phosphorous trichloride, phosphorous acid and dialkyl phosphite and subsequently b) hydrolyzing the product of step a) to form aminomethanephosphonic acid. A mixture of phosphonating agents may be used if desired. Preferred phosphonating agents are phosphorous trichloride, dialkyl chlorophosphinate or a mixture of phosphorous trichloride and an alcohol. An anhydrous solvent may be used with the phosphonating agent.

EP 0537786 patent discloses a process for preparing N-acylaminomethylphosphonic acid from an N-methylolamide compound and a phosphorus trihalide. The starting compounds are mixed and heated in an aprotic solvent in the presence of water in a 0.25 to 2.5 time molar amount relative to the phosphorus trihalide at 60 to 160° C. The N-methylolamide compound is a compound selected from the group consisting of N-methylol-lower alkylamides and N-methylolarylamides. The phosphorus trihalide is preferably phosphorus trichloride. The aprotic solvent is selected among hydrocarbons, halogenated hydrocarbons, ethers, polyethers, nitriles, and aromatic nitro compounds. The mixing may be carried out at a temperature of 60° C. One of the most important requirements of the process is to add a predetermined amount of water to the mixture of the starting compounds (N-methylolamide and phosphorus trihalide) at the initiation of the reaction.

EP 480307 patent discloses a process for the preparation of acylaminomethanephosphonic acids which are useful intermediates for the preparation of the herbicide N-(phosphonomethyl)glycine and its salts. Acylaminomethanephosphonic acids of the formula $R^1$—CO—NH—$CH_2$—$PO_3H_2$ in which $R^1$ is H, $C_1$-$C_6$-alkyl, benzyl or optionally substituted phenyl, can be prepared in an industrial process, which comprises the reaction of the compound of the formula $R^1$—CO—NH—$CH_2$—OH with $P_2O_3$ and its hydrolysis with water. If appropriate a solvent, such as acetic acid, acetonitrile, tetrahydrofuran and dioxane can be used. The molar ratio of N-hydroxymethyl acetamide to $P_2O_3$ is preferably 2:1. The components are mixed in a temperature range from 5° C. to 60° C.; the sequence of the addition of the components is not critical. Thereupon the reaction mixture is heated to a temperature comprised between 60° C. and 200° C. After the reaction is complete the mixture is allowed to cool and is treated with water. To accelerate the hydrolysis, an increase in temperature, for example up to reflux temperature, may be appropriate.

EP 2112156 patent application discloses a method for the manufacture of aminoalkylene phosphonic acid, comprising the steps of adding tetraphosphorus hexaoxide to an aqueous reaction medium containing a homogeneous Brønsted acid, whereby the tetraphosphorus hexaoxide will substantially qualitatively hydrolyse to phosphorous acid, whereby the free water level in the reaction medium, after the hydrolysis of the tetraphosphorus hexaoxide is completed, is in the range of from 0 to 40% by weight. In a subsequent step an amine, formaldehyde and additional Brønsted acid is added to the reaction medium whereupon the reaction is completed to thus yield the aminoalkylene phosphonic acid. In a variant of this process, the amine can be added before or during the tetraphosphorus hexaoxide hydrolysis step.

DE4026026 patent discloses a process for the preparation of acylaminomethanephosphonic acid of formula $R^2$—CO—NH—$CH_2$—P(O)(OH)$R^1$, wherein $R^1$ stands for hydroxy, $C_1$-$C_4$ alkyl or phenyl and $R^2$ stands for $C_1$-$C_6$ alkyl, benzyl or phenyl, which can be substituted by one or more residues chosen from the group consisting of $C_1$-$C_4$ alkyl, $C_1$-$C_4$ alkoxy and halogen. These molecules are useful intermediate products in the preparation of biologically active compounds. They can be prepared by reacting a compound of formula $R^2$—CO—NH—$CH_2$—OH with compounds of formula H—P(O)(OH)$R^1$ in the presence of at least equimolar quantities, referred to the compound of formula $R^2$—CO—NH—$CH_2$—OH, of acetic anhydride.

U.S. Pat. No. 4,422,982 discloses a method for the production of N-(phosphonomethyl)glycine which comprises the steps of: (a) reacting formaldehyde with formamide at a pH of 9-10 to form N-(hydroxymethyl)formamide, (b) reacting N-(hydroxymethyl)formamide with triethylphosphite, in a 1/1 molar ratio at a temperature of approximately 120° C.-125° C. for a period of time comprised between 2 and 3 hours, to form diethyl-N-(formyl)aminomethylphosphonate and ethanol, (c) reacting diethyl-N-(formyl)aminomethylphosphonate with methylchloroacetate, in the presence of a proton extracting base (preferably sodium hydride) and a suitable solvent (preferably tetrahydrofuran), to form N-(diethylphosphonomethyl)-N-(formyl) glycinemethyl ester, and (d) reacting N-(diethylphosphonomethyl)-N-(formyl)glycinemethyl ester with hydrochloric acid to form N-(phosphonomethyl)glycine.

U.S. Pat. No. 4,804,499 discloses a process for the preparation of an N-substituted aminomethylphosphonic acid comprising reacting a 2,5-diketopiperazine compound with phosphorous acid and formaldehyde in an acidic medium.

U.S. Pat. No. 4,400,330 discloses a method for the production of N-phosphonomethylglycine which comprises the steps of first reacting 2,5-diketopiperazine with paraformaldehyde in glacial acetic acid, then adding a halogen substituted phosphorus compound, all in the presence of a low molecular weight carboxylic acid solvent, to form an intermediate N,N'-bisphosphonomethyl-2,5-diketopiperazine compound.

The synthesis of (2S*,3aS*,7aS*)-octahydroindole-2-phosphonic acid starting from cis-octahydroindol-2-one is disclosed by Arizpe et al. in *Eur. J. Org. Chem.* 2011, 3074-3081. The 2-methoxy-octahydroindole obtained from the reaction of the unstable intermediate 2-hydroxy-octahydroindole and methanol, subsequently is reacted with trimethylphosphite in the presence of boron trifluoride diethyl ether to form the octahydroindole-2-phosphonic acid upon treatment with a 33% solution of hydrogen bromide in acetic acid.

The procedure for the synthesis of DL-diethyl pyrrolidine-2-phosphonate and the direct conversion of peptides containing carboxy-terminal proline into the corresponding phosphono analogues, containing phospho-terminal 2-phosphonopyrrolidine, is described by Pagani et al. in *Int. J. Peptide Protein Res.* 34, 1989, 33-36. As reported, the procedure involves the treatment at room temperature of an ethereal solution of carbinolamides with triethylphosphite, in the presence of boron trifluoride ethyl etherate. The carbinolamides are obtained from the corresponding carboxy-activated N-protected amino acids and peptides via oxidative decarboxylation.

The synthesis of dipeptide-derived diaryl isoindolin-1-yl phosphonate is reported by Van der Veken et al. in *J. Med. Chem.* 2007, 50, 5568-5570. In this synthesis, an intermediate step consists in subjecting a cyclic hemiaminal to a modified Birum-Oleksyszyn protocol using either triphenylphosphite or tris(4-acetamidophenyl)phosphate and a Lewis acid catalyst to form diphenyl or bis(4-acetamidophenyl) isoindolin-1-yl phosphonate.

The ureidoalkylation of phosphorus (III) compounds is reported by Petersen et al. in *Liebigs Ann. Chem.* 766, 58-72 (1972). On pages 65 and 72 the reaction of diethylphosphite and 2-oxo-1,3,5,5-tetramethyl-4-hydroxy-hexahydropyrimidine, to form 2-oxo-1,3,5,5-tetra methyl-hexahydro-4-pyrimidyl-phosphonic acid diethylester is described. Hereto the reaction mixture is heated to a temperature of about 90° C.-95° C. while stirring and kept at that temperature for a period of time of about 2 hours. Subsequently water and excess of diethylphosphite is distilled off under vacuum.

The treatment of N-hydroxymethylated lactames of 2,4 diamino-L-butanoic acid, L-ornithine and L-lysine with phosphorus trichloride to give the phosphonic acids and with methyldichlorophosphine to give the methylphosphinic acids is reported by Natchev in *Phosphorus and Sulfur,* 1988, Vol. 37, pp. 143-148. The hydroxymethyl derivatives and phosphorus trichloride are stirred for 1 hour at room temperature and for another 15 minutes at a temperature of about 50° C.-60° C. The resulting reaction products are dissolved in tetrachloromethane and cold acetic acid is added to form the phosphinic acid derivatives. The mixture, after standing for 24 hours at room temperature, is decanted and the resultant mass is recrystallized from water.

AIMS OF THE INVENTION

The present invention aims to provide a new and efficient synthesis of aminoalkylenephosphonic acid or its phosphonate esters that do not present the drawbacks of the methods of the prior art. It is, in particular an aim of the present invention to provide a one step synthesis capable of selectively delivering superior compound grades at high purity and high yield. Another aim of the present invention is to synthesize the phosphonic acid compounds in a shortened and energy efficient manner.

SUMMARY OF THE INVENTION

The present invention discloses a method for the synthesis of an aminoalkylenephosphonic acid or its phosphonate esters, comprising the following steps:

a) forming, in the presence of an aldehyde or ketone and an acid catalyst, a reaction mixture by mixing a compound (a.1.) comprising at least one $HNR^1R^2$ moiety or a salt thereof, with a compound (a.2.) having one or more P—O—P anhydride moieties, said moieties comprising one P atom at the oxidation state (+III) and one P atom at the oxidation state (+III) or (+V), wherein the ratio of moles of aldehyde or ketone to N—H moieties is 1 or more and wherein the ratio of N—H moieties to P—O—P anhydride moieties is 0.3 or more, and wherein:
the $HNR^1R^2$ comprising compound (a.1.) is characterized in that:
- (a.1.1) $R^1$ and $R^2$ are independently selected from the group consisting of hydrogen, $C_1$-$C_6$ alkyl, $C_1$-$C_6$ alkenyl, $C_1$-$C_6$ alkynyl, $C_1$-$C_6$ acyl, optionally comprising an ethylenically unsaturated double bond, and (meth)acryloyl $C_1$-$C_6$ moiety, the $C_1$-$C_6$ part of said moieties being normal chained, branched or cyclised and being optionally substituted by one or more moieties selected from the group consisting of $C_1$-$C_4$ hydrocarbon, aryl and aralkyl and optionally comprising one or more heteroatoms selected from the group consisting of oxygen, nitrogen and sulfur and optionally comprising one or more carbonyl moieties, or
- (a.1.2) $R^1$ and $R^2$ are forming a ring structure wherein N—H is incorporated in said ring and wherein said ring is optionally substituted by one or more moieties selected from the group consisting of $C_1$-$C_4$ hydrocarbon, aryl and aralkyl and optionally comprises one or more heteroatoms selected from the group consisting of oxygen, nitrogen and sulfur and optionally comprises one or more carbonyl moieties, or
- (a.1.3.) $R^1$ and $R^2$ form part of a polymer wherein at least one >NH is incorporated in the polymer chain or wherein at least one $HNR^1$ is a repeating substituent moiety on the polymer chain comprising polymerized $R^2$ moieties optionally copolymerized with other polymerizable monomers, characterized in that $R^1$ an $R^2$ are independently selected from the group consisting of hydrogen, $C_1$-$C_6$ alkyl, $C_1$-$C_6$ alkenyl, $C_1$-$C_6$ alkynyl, $C_1$-$C_6$ acyl, optionally comprising an ethylenically unsaturated double bond, and (meth)acryloyl $C_1$-$C_6$ moiety, the $C_1$-$C_6$ part of said moieties being normal chained, branched or cyclised and being optionally substituted by one or more moieties selected from the group consisting of $C_1$-$C_4$ hydrocarbon, aryl and aralkyl and optionally comprising one or more heteroatoms selected from the group consisting of oxygen, nitrogen and sulfur and optionally comprising one or more carbonyl moieties,
and wherein:
the compounds (a.2.) comprising P—O—P anhydride moieties are selected from the group consisting of:
tetraphosphorus hexaoxide, tetraethylpyrophosphite and the compounds (a.2.) comprising P—O—P anhydride moieties obtained from the combination of one or more compounds comprising:
(a.2.1) one or more P—OH moieties with one or more compounds comprising one or more P—O—P anhydride moieties or one or more P—X moieties, wherein the P atom of one or more compounds is at the oxidation state (+III);
(a.2.2) one or more P—X moieties and water, wherein the P atom of the P—X moiety comprising compound is at the oxidation stage (+III);
(a.2.3) two or more P—O—P moieties and water, wherein the P—O—P moiety comprising compound has a P atom at the oxidation state (+III) and a P atom at the oxidation state (+III) or (+V);
wherein the compounds having one or more P—OH moieties are accessible by tautomerization of a >P(=O)H moiety,
wherein X is a halogenide selected from the group consisting of chlorine, bromine and iodine and
wherein the halogen level in the P—O—P anhydride comprising compound is 1000 ppm or less, preferably 500 ppm or less and more preferably 200 ppm or less
and
b) recovering the resulting compound comprising aminoalkylene phosphonic acid or one of its phosponate esters, Particular embodiments of the present invention disclose one or more of the following features:
the ratio of N—H moieties to P—O—P moieties is comprised between 0.3 and 2.0 and preferably between 0.5 and 1.5;
the reaction of step a) is performed at a temperature comprised between 20° C. and 120° C., preferably between 40° C. and 100° C., for a period of time comprised between 30 minutes and 24 hours, preferably between 1 hour and 20 hours;
the method of the present invention comprises the additional steps of:
adding water to the reaction mixture after completion the conversion of the $HNR^1R^2$ moiety comprising compound into the aminoalkylenephosphonic acid comprising compound;
bringing the reaction mixture comprising the added water, to a temperature comprised between 20° C. and 150° C. and
maintaining the reaction mixture comprising the added water at said temperature for at least 10 minutes.
the compound comprising the P—O—P anhydride moiety is selected from the group consisting of tetraphosphorus hexaoxide, tetraethylpyrophosphite, and the P—O—P anhydride moiety comprising compound obtained from the combination of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water;
the compound comprising the P—O—P anhydride moieties is tetraphosphorus hexaoxide;
the R moiety of the aldehyde with general formula R—CO—H is selected from the group consisting of hydrogen, aliphatic moiety, araliphatic moiety, aromatic moiety and heterocyclic moiety wherein the total number of carbon and hetero atoms is comprised between 1 and 11;
the R' and R" of the ketone with general formula R'—CO—R" are independently selected from the group consisting of aliphatic moiety, araliphatic moiety and aromatic hydrocarbon moiety wherein the total number of carbon atoms is comprised between 1 and 12;
the aldehyde is formaldehyde;
the acid catalyst is a homogeneous Brønsted acid catalyst preferably selected from the group consisting of methanesulfonic acid, trifluoromethanesulfonic acid, trifluoroacetic acid, p-toluenesulfonic acid, hydrochloric acid, phosphorous acid, phosphoric acid and mixtures thereof;
the acid catalyst is a heterogeneous Brønsted acid preferably selected from the group consisting of:
(i) solid acidic metal oxide combinations as such or supported onto a carrier material;
(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;
(iii) organic sulfonic, carboxylic and phosphonic Brønsted acids which are substantially immiscible in the reaction medium at the reaction temperature;
(iv) an acid catalyst derived from:
the interaction of a solid support having a lone pair of electrons onto which is deposited an organic Brønsted acid; or
the interaction of a solid support having a lone pair of electrons onto which is deposited a compound having a Lewis acid site; or
heterogeneous solids functionalized by chemical grafting with a Brønsted acid group or a precursor therefore; and
(v) heterogeneous heteropolyacids of the general formula $H_xPM_yO_z$ wherein P is selected from phosphorus and silicon and M is selected from tungsten and molybdenum and combinations thereof;
the acid catalyst is a homogeneous Lewis acid preferably selected from the group consisting of $LiN(CF_3SO_2)_2$, $Mg(OCF_3SO_2)_2$, $Al(OCF_3SO_2)_3$, $Bi(OCF_3SO_2)_3$, $Sc(OCF_3SO_2)_3$;
the acid catalyst is a heterogeneous Lewis acid obtained from the interaction of a homogeneous Lewis acid catalyst and an organic or inorganic polymer compound;
step a) comprises a solvent selected from the group consisting of 1,4-dioxane, toluene, ethylacetate, acetonitrile, acetic acid, sulfolane, 1-ethyl-3-methyl-imidazolium bis(trifluoromethylsulfonyl)imide, or a mixture thereof;
the method of the present invention comprises the steps of:
a) forming a reaction mixture by mixing a compound comprising at least one $HNR^1R^2$ moiety, with an aldehyde or a ketone and an acid catalyst optionally in the presence of a solvent, to form a compound comprising at least one aminoalkylol moiety;
b) adding a compound comprising at least one P—O—P anhydride moiety, having one P atom at the oxidation state (+III) and one P atom at the oxidation state (+III) or (+V), to the reaction mixture of step a), comprising at least one aminoalkylol moiety, to form a compound comprising aminoalkylene phosphonic acid;
c) adding water to the reaction mixture of step b)
d) recovering the resulting compound comprising aminoalkylenephosphonic acid or one of its phosphonate esters;

the hydrolysis, after completion of the formation of the compound comprising aminoalkylenephosphonic acid, is performed at a pH comprised between 4.0 and 7.0;

the hydrolysis, after completion of the formation of the compound comprising aminoalkylenephosphonic acid, is performed at a temperature comprised between 20° C. and 150° C., preferably between 40° C. and 100° C., for a period comprised between 10 minutes and 72 hours and preferably between 1 hour and 10 hours;

the compound comprising aminoalkylenephosphonic acid, or its phosphonate esters, obtained from the method of the present invention, are used as a phytotoxicant, a scale inhibitor, a dispersing agent and/or a sequestering agent.

DETAILED DESCRIPTION OF THE INVENTION

The present invention provides an efficient and economical method for the synthesis of aminoalkylenephosphonic acid or its phosphonate esters with high selectivity and high yield.

The phosphonate esters of the present invention comprise one or more substituted or unsubstituted hydrocarbyl groups which may be branched or unbranched, saturated or unsaturated, and may contain one or more rings. Suitable hydrocarbyls include alkyl, alkenyl, alkynyl and aryl moieties. They also include alkyl, alkenyl, alkynyl and aryl moieties substituted with other aliphatic or cyclic hydrocarbyl groups, such as alkaryl, alkenaryl and alkynaryl.

The substituted hydrocarbyl is defined as a hydrocarbyl wherein at least one hydrogen atom has been substituted with an atom other than hydrogen such as an halogen atom (F, Cl, Br and I), an oxygen atom to form for example an ether or an ester, a nitrogen atom to form an amide or nitrile group or a sulfur atom to form for example a thioether group.

Phosphonate esters in general are prepared by using the P—O—P anhydride moiety comprising compound substituted with the corresponding hydrocarbyl substituents.

The present method includes an arrangement whereby a compound comprising a P—O—P anhydride moiety, having one P atom at the oxidation state (+III) and the other P atom at the oxidation state (+III) or (+V), ammonia, or a primary or secondary amine and an aldehyde or a ketone are reacted in the presence of an acid catalyst and optionally a solvent.

While the P—O—P anhydride moiety comprising compound is preferably selected from the group consisting of tetraphosphorus hexaoxide and partially hydrolysed species of tetraphosphorus hexaoxide obtained through reaction of 1 mole of tetraphosphorus hexaoxide with 1, 2, 3, 4 and 5 moles of water respectively, it is understood that all compounds comprising at least one P—O—P anhydride group wherein one P atom is at the oxidation state (+III) and the other P atom is at the oxidation state (+III) or (+V) can be used for the purpose of the present invention.

Suitable P—O—P anhydride moiety comprising compounds can either comprise a P—O—P anhydride moiety in the compound itself (e.g. $P_4O_6$ or pyrophosphites $(RO)_2P$—O—$P(OR)_2$) or can be generated in situ by combining reagents that will form the required P—O—P anhydride moiety upon combination before reacting with the aminoalkylol.

Suitable reagent combinations are:

a) compounds containing a least one P—OH moiety (also accessible by tautomerisation of a >P(=O)H moiety into >P(LP)OH (where LP stands for lone pair of electrons), such as for example is the case for dimethylphosphite $(MeO)_2P$(=O)H), and compounds containing at least one P—O—P anhydride moiety e.g. $P_2O_5$ or $P_4O_6$;

b) compounds containing at least one P—OH moiety and compounds containing at least one P—X (X=Cl, I, Br) moiety;

c) compounds containing at least one P—X moiety and $H_2O$;

d) compounds containing P—O—P anhydride moieties and $H_2O$ for partial hydrolysis In case a) and b) it is mandatory that at least in one of the utilised compounds the P atom is in the oxidation state (+III) whereas in case c) the P atom has to be in the oxidation state (+III) and in case d) the P—O—P moieties have one P atom at the oxidation state (+III) and the other P atom at the oxidation state (+III) or (+V), in order to form the P—O—P anhydride moiety comprising compound, having one P atom at the oxidation state (+III) and the other P atom at the oxidation state (+III) or (+V).

P—O—P anhydride moiety comprising compounds wherein the P—O—P anhydride moiety is already present are phosphorus oxides with the formula $P_4O_n$ with n=6-9, pyrophosphites with the general formula $(RO)_2P$—O—$P(OR)_2$ wherein R is an alkyl or aryl group, pyrophosphorous acid $(H_4P_2O_5)$ and isohypophosphoric acid (H)(HO)P(O)—O—P(O)(OH)$_2$.

Combinations described under a) are obtained by reacting e.g. phosphorus oxides with formula $P_4O_n$ with n=6-10, alkyl substituted pyrophosphites, pyrophosphorous acid, isohypophosphoric acid, metaphosphoric acid or polyphosphoric acid with phosphorous acid, phosphoric acid, mono or disubstituted phosphites with formula $(RO)PO_2H_2$ or $(RO)_2POH$ wherein R is an alkyl or aryl group, phosphate esters $(RO)PO_3H_2$ or $(RO)_2PO_2H$, phosphonic acids $RPO_3H_2$ or its monoester $RPO_2H(OR)$ with the proviso that such combinations will lead to P—O—P anhydride moiety comprising compounds having one P atom at the oxidation state (+III) and the other P atom at the oxidation state (+III) or (+V).

Combinations described under b) are obtained by combining $PCl_3$, $PBr_3$, $POCl_3$ or mono or dichloro phosphites like $(RO)_2PCl$ and $(RO)PCl_2$ with phosphorous acid, phosphoric acid or mono or disubstituted phosphites with formula $(RO)PO_2H_2$ or $(RO)_2POH$ with the proviso that such combinations will lead to P—O—P anhydride moiety comprising compounds having one P atom at the oxidation state (+III) and the other P atom at the oxidation state (+III) or (+V).

Combinations described under c) are obtained by combining $PCl_3$, $PBr_3$ or mono or dichloro phosphites like $(RO)_2PCl$ and $(RO)PCl_2$ with $H_2O$.

In order to obtain a P—O—P anhydride moiety comprising compounds free of P—X functions the remaining P—X functions are hydrolysed. Remaining P—O—P anhydride moieties can also be hydrolysed as long as the required P—O—P anhydride moiety wherein one P atom is at the oxidation state (+III) and the other P atom is at the oxidation state (+III) or (+V) remains.

Most preferred are tetraphosphorus hexaoxide, tetraethylpyrophosphite and the combinations of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water.

The amount of 'reactive' P(+III) atoms that can be converted into phosphonic acids according to this invention is determined by the amount of P(+III) atoms and the amount of P—O—P anhydride moieties. If there are more P—O—P anhydride moieties than P(+III) atoms, then all P(+III) atoms are converted into phosphonic acids. If there are less P—O—P anhydride moieties than P(+III) atoms then only a part of P(+III) atoms, equal to the amount of P—O—P anhydride moieties, is converted into phosphonic acids.

If halogen containing starting materials, e.g. $PCl_3$, $POCl_3$ or $PBr_3$ are used, the level of halogen in the P—O—P anhydride comprising compound shall be kept below 1000 ppm, usually below 500 ppm, preferably below 200 ppm, expressed in relation to the P—O—P material being 100%. Therefore all excess P—X functions are hydrolysed, before the reactions with the substrate, by addition of one molecule of $H_2O$ per excess of P—X function. The formed H—X is removed by e.g. blowing a dry inert gas, like nitrogen or helium, through the solution.

The tetraphosphorus hexaoxide preferably used within the scope of the present invention may be represented by a substantially pure compound containing at least 85%, preferably more than 90%, more preferably at least 95% and in one particular execution at least 97% of $P_4O_6$. While tetraphosphorus hexaoxide, suitable for use within the context of this invention, may be manufactured by any known technology, in preferred executions it is prepared in accordance with the method described in WO 2009/068636 and/or WO 2010/055056 patent applications under the section entitled "Process for the manufacture of $P_4O_6$ with improved yield". In detail, oxygen, or a mixture of oxygen and inert gas, and gaseous or liquid phosphorus are reacted in essentially stoichiometric amounts in a reaction unit at a temperature in the range from 1600 K to 2000 K, by removing the heat created by the exothermic reaction of phosphorus and oxygen, while maintaining a preferred residence time of from 0.5 seconds to 60 seconds followed by quenching the reaction product at a temperature below 700 K and refining the crude reaction product by distillation. The tetraphosphorus hexaoxide so prepared is a pure product containing usually at least 97% of the oxide. The so produced $P_4O_6$ is generally represented by a liquid material of high purity containing in particular low levels of elementary phosphorus, $P_4$, preferably below 1000 ppm, expressed in relation to the $P_4O_6$ being 100%. The preferred residence time is from 5 seconds to 30 seconds, more preferably from 8 seconds to 30 seconds. The reaction product can, in one preferred execution, be quenched to a temperature below 350 K.

It is presumed that the $P_4O_6$ participating in a reaction at a temperature of from 24° C. (melting t°) to 120° C. is necessarily liquid or gaseous although solid species can, academically speaking, be used in the preparation of the reaction medium.

For reasons of convenience and operational expertise, the tetraphosphorus hexaoxide, represented by $P_4O_6$, is of high purity and contains very low levels of impurities, in particular elemental phosphorus, $P_4$, at a level below 1000 ppm, usually below 500 ppm and preferably not more than 200 ppm, expressed in relation to the $P_4O_6$ being 100%.

In the present invention it is understood that when using the terminology "P—O—P anhydride moiety comprising compound" it is meant "P—O—P anhydride moiety comprising compound wherein one P atom is at the oxidation state (+III) and the other P atom is at the oxidation state (+III) or (+V)

The $HNR^1R^2$-comprising compound, used in the present invention, can be a low molecular weight organic molecule or form part of a polymer wherein the low molecular weight organic molecule or the polymer may be grafted on inorganic material.

For the $HNR^1R^2$ comprising compound being a low molecular weight organic molecule, it is further characterized in that:
$R^1$ and $R^2$ are independently selected from hydrogen, $C_1$-$C_6$ alkyl, $C_1$-$C_6$ alkenyl, $C_1$-$C_6$ alkynyl, $C_1$-$C_6$ acyl, optionally comprising an ethylenically unsaturated double bond, and (meth)acryloyl $C_1$-$C_6$ moiety, wherein the $C_1$-$C_6$ part of said moieties is normal chained, branched or cyclised and is optionally substituted by one or more moieties selected from the group consisting of $C_1$-$C_4$ hydrocarbon, aryl and aralkyl and optionally comprises one or more heteroatoms selected from the group consisting of oxygen, nitrogen and sulfur and optionally comprises one or more carbonyl moieties.

$R^1$ and $R^2$ may form a ring structure wherein N—H is incorporated in said ring and wherein said ring is optionally substituted by one or more moieties selected from the group consisting of $C_1$-$C_4$ hydrocarbon, aryl and aralkyl and optionally comprises one or more heteroatoms selected from the group consisting of oxygen, nitrogen and sulfur and optionally comprises one or more carbonyl moieties.

For the $HNR^1R^2$ comprising compound forming part of a polymer, at least one >N—H is incorporated in the polymer chain or at least one —$NHR^1$ is a repeating substituent moiety on the polymer chain comprising polymerized $R^2$ moieties, optionally copolymerized with other polymerizable monomers.

The $HNR^1R^2$ comprising compound forming part of a polymer is further characterized in that $R^1$ and $R^2$ are independently selected from the group consisting of:
hydrogen, $C_1$-$C_6$ alkyl, $C_1$-$C_6$ alkenyl, $C_1$-$C_6$ alkynyl, $C_1$-$C_6$ acyl comprising at least 1 ethylenically unsaturated double bond, and (meth)acryloyl) $C_1$-$C_6$ moiety, wherein the $C_1$-$C_6$ part of said moieties is normal chained, branched or cyclised and is optionally substituted by one or more moieties selected from the group consisting of $C_1$-$C_4$ hydrocarbon, aryl and aralkyl and optionally comprises one or more heteroatoms selected from the group consisting of oxygen, nitrogen and sulfur and optionally comprises one or more carbonyl moieties.

The aldehyde, with general formula R—CO—H, for being used in the method of the present invention, is selected from the compounds in which R is an hydrogen, an aliphatic, araliphatic, aromatic or heterocyclic moiety and in which the total number of carbon and hetero atoms assumes preferably a value of from 1 to 11. Aliphatic moieties are especially alkyl moieties, preferable those with 1 to 6 carbon atoms, examples being methyl, ethyl, propyl, butyl. The aliphatic moieties can also be branched, examples being isobutyl. Aromatic moieties are for example phenyl or α- or β-naphtyl and heterocyclic moieties are for example furfuryl. The aldehyde can also have one or more substituents, such as for example the alkoxy group.

Examples of aldehydes with saturated aliphatic moieties are formaldehyde, acetaldehyde and butyraldehyde. Examples of aldehydes with substituted saturated aliphatic moieties are methoxyacetaldehyde and 3-methoxypropionaldehyde. Examples of aldehydes with araliphatic moieties are phenylacetaldehyde and phenylpropionaldehyde. Examples of aldehydes with aromatic or heterocyclic moieties are benzaldehyde, furfural and 4-methoxyfurfural.

The ketone, with general formula R'—CO—R", for being used in the method of the present invention is a symmetrical or asymmetrical compound with R' and R" being independently selected from aliphatic, araliphatic, cyclic or aromatic hydrocarbon moieties, the total number of carbon atoms assuming preferably a value of from 1 to 12. The aliphatic moieties are straight-chain or branched and preferably saturated alkyl moieties such as for example methyl, ethyl, propyl and isobutyl. Araliphatic moieties are for example benzyl or phenethyl and aromatic moieties are for example α- or β-naphtyl and preferably phenyl. The ketones can also have one or more substituents such as for example the alkoxy group.

Examples of ketones with saturated aliphatic moieties are acetone, methylethylketone, methylisobutylketone; examples of ketones with substituted aliphatic moieties are methoxyacetone. An example of ketones with araliphatic moieties is benzylacetone; examples of ketones with cyclic moieties are cyclohexanone and cyclopentanone while examples of ketones with aromatic moieties are acetophenone and 4-methoxy-acetophenone.

Formaldehyde is used with special preference as aldehyde. Formaldehyde known as oxymethylene having the formula $CH_2O$ is produced and sold as water solutions containing variable, frequently minor, e.g. 0.3-3%, amounts of methanol and are typically reported on a 37% formaldehyde basis although different concentrations can be used. Formaldehyde solutions exist as a mixture of oligomers. Such formaldehyde precursors can, for example, be represented by paraformaldehyde, a solid mixture of linear poly (oxymethylene glycols) of usually fairly short, n=8-100, chain length, and cyclic trimer of formaldehyde designated by the terms 1,3,5-trioxane. Concentrations of liquid formaldehyde above about 37% need to be kept above room temperature to prevent the precipitation of formaldehyde polymers. The temperature necessary to maintain a clear solution and prevent separation of solid polymer increases from room temperature as the solution concentration is increased above about 37%.

While formaldehyde is preferably added as 37% by weight solution in water, known as formalin, it also can be added as an aqueous solution with a formaldehyde concentration different from 37% by weight or as a solid such a for example as paraformaldehyde or as 1,3,5-trioxane.

When formaldehyde is used as an aqueous solution, it goes without saying that the aminoalkylol intermediate first has to be isolated before it is put into reaction with the P—O—P anhydride moiety comprising compound with the proviso that the step of isolating the aminoalkylol can be omitted for those cases where the water quantities, present in the aqueous formaldehyde solution are in accordance with those required for transforming a first P—O—P anhydride moiety comprising compound into a modified P—O—P-anhydride moiety comprising compound through partially hydrolysis of said first P—O—P anhydride moiety comprising compound whereupon said modified PO—P anhydride moiety comprising compound will react with the aminoalkylol to form aminoalkylenephosphonic acid.

The acid catalyst used within the scope of the present invention is preferably a homogeneous Brønsted acid catalyst, optionally in the presence of a solvent, or a heterogeneous Brønsted acid catalyst, in the presence of a solvent, or a Lewis acid catalyst, in the presence of a solvent.

The homogeneous Brønsted acid preferably is selected from the group consisting of methanesulfonic acid, fluoromethanesulfonic acid, trichloromethanesulfonic acid, trifluoromethanesulfonic acid, trifluoroacetic acid, tert-butylsulfonic acid, p-toluenesulfonic acid, naphthalene sulfonic acid, 2,4,6-trimethylbenzene-sulfonic acid, perfluoro or perchloro alkyl sulfonic acids, perfluoro or perchloro alkyl carboxylic acids, hydrochloric acid, hydrobromic acid, hydroiodic acid, phosphorous acid, phosphoric acid, and mixtures thereof. The homogeneous Brønsted acid is preferably methanesulfonic acid.

The heterogeneous Brønsted acid is preferably selected from the group consisting of:

(i) solid acidic metal oxide combinations as such or supported onto a carrier material;

(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;

(iii) organic sulfonic, carboxylic and phosphonic Brønsted acids which are substantially immiscible in the reaction medium at the reaction temperature;

(iv) an acid catalyst derived from:
the interaction of a solid support having a lone pair of electrons onto which is deposited an organic Brønsted acid; or
the interaction of a solid support having a lone pair of electrons onto which is deposited a compound having a Lewis acid site; or
heterogeneous solids functionalized by chemical grafting with a Brønsted acid group or a precursor therefore; and (v) heterogeneous heteropolyacids of the general formula $H_xPM_yO_z$ wherein P is selected from phosphorus and silicon and M is selected from tungsten and molybdenum and combinations thereof.

Preferred homogeneous Lewis acids can be selected from metal salts having the general formula:

$$MX_n$$

wherein M represents a main group element or transition metal like Li, B, Mg, Al, Bi, Fe, Zn, La, Sc, Yb, or Pd; X in $MX_n$ is typically an anion of an acid or acid derivative like Cl, OTf or $NTf_2$, where Tf stands for $CF_3SO_2$ and n is equal to the oxidation state of M, which can be from 1 to 5. Possible combinations are e.g. $LiNTf_2$, $Mg(OTf)_2$, $MgCl_2$, $ZnCl_2$, $PdCl_2$, $Fe(OTf)_3$, $Al(OTf)_3$, $AlCl3$, $Bi(OTf)_3$, $BiCl_3$, $Sc(OTf)_3$, $Ln(OTf)_3$, $Yb(OTf)_3$. Preferably, combinations of a hard metal or a metal on the borderline between hard and soft according to the HSAB (hard soft acid base) concept like Li, Mg, Al, Sc, Zn, Bi, and weakly coordinating anions like OTf or $NTf_2$ are used. Examples of such preferred combinations are $LiNTf_2$, $Mg(OTf)_2$, $Al(OTf)_3$, $Bi(OTf)_3$.

Preferred heterogeneous Lewis acids can be represented by species of discretionary selected subclasses created by interaction/bonding of homogeneous Lewis acids e.g. metal complexes, metal salts or organometallic species with polymeric organic or inorganic backbones. An example of such subclass is a polystyrene matrix with bonded $Sc(OTf)_2$ groups. Such catalyst can be prepared e.g. by interaction of a polystyrene sulfonic acid resin, e.g. Amberlyst 15, with $Sc(OTf)_3$. The number of equivalents of Lewis acid functions can be determined in this case by different ways e.g. by acid base determination of the unreacted sulfonic acid groups, by quantitative determination of the liberated triflic acid and by ICP measurement of the amount of Sc on the resin.

Typical examples of suitable organic solvents to be used in the method of the invention are anisole; acetic acid; chlorinated and fluorinated hydrocarbons, such as fluorobenzene, chlorobenzene, tetrachloroethane, tetrachloroethylene, dichloroethane, dichloromethane; polar solvents like diglyme, glyme, diphenyloxide, polyalkylene glycol derivatives with capped OH groups such as OR* where R* is a low alkyl or acyl group; aliphatic hydrocarbons such as hexane, heptane, cyclohexane; non-cyclic ethers like dibutyl ether, diethyl ether, diisopropyl ether, dipentylether and butylmethylether; cyclic ethers like tetrahydrofuran, dioxane, and tetrahydropyran; mixed cyclic/non-cyclic ethers like cyclopentylmethylether; cyclic and non-cyclic sulfones like sulfolane; aromatic solvents like toluene, benzene, xylene; organic acetates like ethylacetate; organic nitriles like acetonitrile, benzonitrile; silicon fluids like polymethylphenyl siloxane; non-reactive ionic liquids like 1-n-butyl-imidazolium trifluoromethanesulfonate, and 1-ethyl-3-methyl-imidazolium bis(trifluoromethylsulfonyl) imide.

In a particular embodiment of the present invention the acid catalyst acts as catalyst and as solvent.

The method of the present invention is started by mixing the $HNR^1R^2$ comprising compound, the P—O—P anhydride moiety comprising compound, preferable tetraphosphorus hexaoxide, and the aldehyde or ketone, preferable formaldehyde, in the presence of an acid catalyst and optionally a solvent,
  the ratio of equivalents of >N—H moieties to moles of aldehyde or ketone is comprised between 0.9 and 1.5 and preferably between 1.1 and 1.4;
  the ratio of equivalents of >N—H moieties to P—O—P anhydride moieties is comprised between 0.3 and 2.0 and preferably between 0.5 and 1.5.

In the present invention, the method may comprise the steps of forming a reaction mixture by the alternating gradual addition of aldehyde or ketone, preferable formaldehyde, and the P—O—P anhydride moiety comprising compound, preferable tetraphosphorus hexaoxide, in portions, to the $HNR^1R^2$ comprising compound in the presence of an acid catalyst and optionally a solvent.

In a particular embodiment of the present invention the method comprises the steps of forming a reaction mixture by mixing the $HNR^1R^2$ comprising compound and the P—O—P anhydride moiety comprising compound, preferable tetraphosphorus hexaoxide, in the presence of a acid catalyst and optionally a solvent; subsequently the aldehyde or ketone, preferable formaldehyde, is gradually added to the reaction mixture (Example 19).

In general the reaction is performed at a temperature comprised between 20° C. and 120° C. and preferably between 50° C. and 110° C. for a period of time comprised between 30 minutes and 24 hours In the present invention, the method may comprise the steps of forming a reaction mixture by mixing an aldehyde or ketone, preferable formaldehyde, and the $HNR^1R^2$ comprising compound in the presence of an acid catalyst and optionally a solvent; subsequently the P—O—P anhydride moiety comprising compound, preferable tetraphosphorus hexaoxide, is gradually added to the reaction mixture (Example 12 and 13, Example 14 to 18 and Example 20).

In the present invention, the method may also comprise the steps of forming a reaction mixture by mixing an aldehyde or ketone, preferable formaldehyde, and the $HNR^1R^2$ comprising compound in the presence of an acid catalyst and optionally a solvent; isolating an optionally purifying the aminoalkylol moiety comprising compound and subsequently gradually adding the P—O—P anhydride moiety comprising compound, preferable tetraphosphorus hexaoxide, to the amino alkylol moiety comprising compound in the presence of an acid catalyst and optionally a solvent (Example 1 to 11).

In general, the addition of an aldehyde or ketone, preferably formaldehyde, to the reaction mixture is performed at a temperature comprised between about 20° C. and about 120° C. and preferably between about 40° C. and about 100° C. and, after completion of the aldehyde or ketone addition, the reaction mixture is kept at that temperature, for a period of time comprised between about 10 minutes and about 24 hours and preferably between about 1 hour and about 20 hours.

In general, the addition of the P—O—P anhydride moiety comprising compound, preferably tetraphosphorus hexaoxide to the reaction mixture is performed at a temperature comprised between about 20° C. and about 120° C. and preferably between about 40° C. and about 100° C. and, after the completion of the tetraphosphorus hexaoxide addition, the reaction mixture is kept at that temperature for a period of time comprised between about 10 minutes and about 24 hours and preferably between about 1 hour and about 20 hours.

After completion of the conversion of the $HNR^1R^2$ comprising compound into aminoalkylenephosphonic acid comprising compound, water is optionally added to the reaction mixture in order to hydrolyse the unreacted P—O—P anhydride moieties, if present and optionally to convert the aminoalkylene phosphonic acid comprising compound or its dehydrated forms or their phosphonate esters in its hydrolysed form, such as in Example 14 to 17 where N-phosphonomethyl-2,5-oxazolidinedione is hydrolysed into N-(phosphonomethyl)glycine with the formation of carbon dioxide or in Example 11 where N,N'-bis(phosphonomethyl) urea is hydrolysed into aminomethylphosphonic acid with the formation of carbon dioxide.

The hydrolysis is performed at a temperature comprised between about 20° C. and about 150° C., preferably between about 40° C. and about 100° C., for a period comprised between about 10 minutes and about 72 hours and preferably between about 1 hour and about 10 hours.

Unreacted P—O—P anhydride moieties may be the result of an incomplete conversion or of the addition of an excess of P—O—P anhydride group comprising compounds, forming the reaction mixture.

For the case of a substantial complete conversion and a stoichiometric loading of the reactants, the addition of water and thus the hydrolysis step can be omitted.

The hydrolysis preferably is performed for a reaction mixture standing at a pH comprised between 4 and 7 what in general is obtained through the addition of an alkali hydroxides, preferable sodium or potassium hydroxide.

EXAMPLES

The following illustrative examples are meant to exemplify but are not destined to limit the scope the present invention.

Example 1

In a round-bottom flask equipped with a mechanical stirrer, a thermometer and a condenser 3.56 g (40 mmole) N-hydroxymethylacetamide was mixed with 10 ml acetonitrile. Slowly, 2.20 g (10 mmole) $P_4O_6$ was added. Afterwards the reaction mixture was heated to 80° C. for 1 hour. Then 0.15 g (1 mmole) trifluoromethanesulfonic acid was added and stirring was continued for 2 hours at 80° C. All volatiles were removed in vacuum and the residue was dissolved in 5 ml $H_2O$ and 10 ml NaOH solution (50% w/w in $H_2O$) and heated to 100° C. for 2 hours. The obtained solution was analysed by $^{31}$P-NMR spectroscopy. Aminomethylphosphonic acid was detected at 15.5% w/w.

Example 2

Using the equipment of Example 1, 1.77 g (10 mmole) of N-hydroxymethylphthalimide was mixed with 8.5 ml of methanesulfonic acid at 60° C. under N2. Slowly, 0.285 ml (2.5 mmole) of $P_4O_6$ was added. Afterwards the reaction mixture was heated at 85° C. overnight. Then 3 ml of water were added and the mixture was heated for 1 hour at 80° C. The solution was diluted with water and brought to pH 5.4 by addition of sodium hydroxide. The mixture was analysed by $^1$H- and $^{31}$P-NMR spectroscopy. N-Phthalimidomethylphosphonic acid was detected at 11.5% w/w.

In table 1 a series of examples, prepared according to the method of the present invention and using the equipment and the method of Example 1 and Example 2, are reported. In this table:
Column 1: indicates the identification number of the example.
Column 2: indicates the type of aminoalkylol moiety comprising compound put into reaction with tetraphosphorus hexaoxide.
Column 3: indicates the number of mmoles of aminoalkylol moiety comprising compound with into brackets the number of aminoalkylol milliequivalents.
Column 4: indicates the type of acid catalyst and of solvent used.
Column 5: indicates the number of mmoles of acid catalyst.
Column 6: indicates the number of mmoles of tetraphosphorus hexaoxide.
Column 7: indicates the ratio of mmoles of aminoalkylol comprising compound to mmoles of tetraphosphorus hexaoxide with into brackets the ratio of aminoalkylol milliequivalents to the mmoles of tetraphosphorus hexaoxide.
Column 8: indicates the ratio of mmoles of acid catalyst to mmoles of aminoalkylol moiety comprising compound with into brackets the ratio of mmoles of acid catalyst to the milliequivalents of aminoalkylol moieties.
Column 9: indicates the ratio of mmoles of acid catalyst to mmoles of tetraphosphorus hexaoxide.
Column 10: indicates the temperature (° C.) at which the mixing of the $HNR^1R^2$ moiety comprising compound, the aldehyde and the P—O—P anhydride comprising compound, in the presence of a solvent, is performed.
Column 11: indicates the temperature (° C.) and time (hours) conditions of the reaction mixture once all the components have been added.
Column 12: indicates the temperature (° C.) and time (hours) conditions of the hydrolysis.
Column 13: indicates the reaction yield, in % by weight, as measured by $^1$H-NMR and $^{31}$P-NMR spectroscopy.
The aminomethylenephosphonic acid moiety comprising compound prepared in the examples of table 1 are:
Example 1: aminomethylphosphonic acid
Example 2 and 3: N-phthalimidomethylphosphonic acid
Example 4: N-phosphonomethyl, N'-phenyl hydantoin
Example 5: N-phosphonomethyloxazolidinone
Example 6 to 10: N-phosphonomethylpyrrolidinone
Example 11: N,N'-bis(phosphonomethyl)urea further hydrolised into aminomethylphosphonic acid Example 12

Using the equipment of Example 1, 1 equivalent of glycine methyl ester hydrochloride was mixed with 1.5 equivalents of paraformaldehyde in 18.5 equivalents of methanesulfonic acid at 50° C. for 1 hour and then at 75° C. for 25 minutes under N2. The temperature was adjusted to 25° C. before the slowly addition of 0.25 equivalent of $P_4O_6$ while keeping the temperature of the reaction medium under 35° C. Afterwards the reaction mixture was heated to 60° C. for 1 hour. Then 30 equivalents of water were added and the mixture was heated at 110° C. for 30 minutes. The solution was diluted with water and brought to pH 5.4. The mixture was analysed by $^{31}$P-NMR spectroscopy. N-(Phosphonomethyl)glycine was detected at 5.2% mol.

Example 13

Using the equipment of Example 1, 0.8 equivalent of N-(2-aminoethyl)ethane-1,2-diamine was mixed with 5.35 equivalents of paraformaldehyde in acetonitrile containing 5 equivalents of trifluoroacetic acid. The mixture was stirred for 40 minutes at 65° C. under N2. The reaction medium was cooled to 35° C. and 1.0 equivalent of $P_4O_6$ was slowly added while the temperature was maintained below 35° C. Afterwards the reaction mixture was heated to 60° C. for 20 minutes. Then an excess of water was added and the mixture was heated at 85° C. for 15 minutes. The solution was diluted with water and brought to pH 5.4. The mixture was analysed by $^{31}$P-NMR spectroscopy. Diethylenetriamine penta(methylenephosphonic acid) was detected at 10% mole.

Example 14

Using the equipment of Example 1, 0.30 g (9.9 mmole) paraformaldehyde was mixed with 8 ml trifluoroacetic acid. Subsequently the reaction mixture was heated to 50° C. and 1.00 g (9.9 mmole) 2,5-oxazolidinedione was added. Afterwards the reaction mixture was stirred for 1 hour at 50° C. Slowly, 0.55 g (2.5 mmole) $P_4O_6$ was added and stirring was continued for 24 hours at 50° C. 10 ml $H_2O$ was added and stirring was continued for 72 hours at 50° C. The obtained solution was analysed by $^1$H- and $^{31}$P-NMR spectroscopy. N-(phosphonomethyl)glycine was detected 42.5% w/w.

Example 15

Using the equipment of Example 1, 1.00 g (9.9 mmole) 2,5-oxazolidinedione was mixed with 8 ml trifluoroacetic acid. Subsequently 0.30 g (9.9 mmole) paraformaldehyde was added. Afterwards the reaction mixture was stirred for 24 hours at ambient temperature. Then the temperature was increased to 50° C. and slowly 0.55 g (2.5 mmole) $P_4O_6$ was added. Stirring was continued for 24 hours at 50° C. 10 ml $H_2O$ was added and stirring was continued for 72 hours at 50° C. The obtained solution was analysed by $^1$H- and $^{31}$P-NMR spectroscopy. N-(phosphonomethyl)glycine was detected 44.7% w/w.

Example 16

Using the equipment of Example 1, 1.00 g (9.9 mmole) 2,5-oxazolidinedione was mixed with 8 ml trifluoroacetic acid. Subsequently 0.30 g (9.9 mmole) paraformaldehyde was added. Afterwards the reaction mixture was stirred for 1 hour at ambient temperature. Slowly, 0.55 g (2.5 mmole) $P_4O_6$ was added. Stirring was continued for 24 hours at 60° C. 10 ml $H_2O$ was added and stirring was continued for 8 hours at 60° C. The obtained solution was analysed by $^1$H- and $^{31}$P-NMR spectroscopy. N-(phosphonomethyl)glycine was detected 34.9% w/w.

Example 17

Using the equipment of Example 1, 1.00 g (9.9 mmole) 2,5-oxazolidinedione was mixed with 8 ml toluene. Subsequently 0.30 g (9.9 mmole) paraformaldehyde was added. Afterwards the reaction mixture was stirred for 3 hours at 80° C. Slowly 1 ml methanesulfonic acid and 0.55 g (2.5 mmole) $P_4O_6$ were added. Stirring was continued for 5 hours at 60° C. 10 ml $H_2O$ was added and stirring was continued for 8 hours at 60° C. The aqueous solution was analysed by $^1$H- and $^{31}$P-NMR spectroscopy. N-(Phosphonomethyl)glycine was detected 5.6% w/w.

Example 18

Using the equipment of Example 1, 7.36 g (245.2 mmole) paraformaldehyde was mixed with 64 ml methanesulfonic acid. Subsequently the reaction mixture was heated to 40° C. and 3.69 g (61.5 mmole) ethylenediamine was added slowly. Afterwards the reaction mixture was heated to 50° C. and 13.55 g (61.6 mmole) $P_4O_6$ was added slowly. The reaction mixture was heated to 85° C. for 1 hour. At ambient temperature 35 ml $H_2O$ was added and the obtained solution and the solid were analysed by $^{31}$P-NMR spectroscopy. Ethylenediamine-tetramethylenephosphonic acid was detected at 36.6% w/w.

Example 19

Using the equipment of Example 1, 11.08 g (184.4 mmole) ethylenediamine was mixed with 64 ml methanesulfonic acid. Subsequently the reaction mixture was heated to 70° C. and 40.64 g (184.7 mmole) $P_4O_6$ was added slowly. Afterwards the reaction mixture was heated to 105° C. and 60.4 g (735.5 mmole) paraformaldehyde solution (36.6% w/w in $H_2O$) was added over 30 minutes. The reaction mixture was heated to 105° C. for 1 hour. At ambient temperature 25 ml $H_2O$ was added and the obtained solution and the solid were analysed by $^{31}$P-NMR spectroscopy. Ethylenediamine-tetramethylenephosphonic acid was detected at 57.5% w/w.

Example 20

Using the equipment of Example 1, 7.36 g (245.2 mmole) paraformaldehyde was mixed with 64 ml methanesulfonic acid. Subsequently the reaction mixture was heated to 40° C. and 3.69 g (61.5 mmole) ethylenediamine was added slowly. Afterwards the reaction mixture was heated to 55° C. and 13.55 g (61.6 mmole) $P_4O_6$ was added slowly. The reaction mixture was heated to 80° C. for 3 hours. At ambient temperature 35 ml $H_2O$ was added and the obtained solution and the solid were analysed by $^{31}$P-NMR spectroscopy. Ethylenediamine-tetramethylene phosphonic acid was detected at 31.9% w/w.

Example 21

Using the equipment of Example 1, 4.24 g (40.0 mmole) benzaldehyde, 3.48 (40.0 mmole) morpholine and 0.12 g (0.8 mmole) trifluoromethanesulfonic acid were mixed with 10 ml 1,4-dioxane. Subsequently, the reaction mixture was stirred for 48 hours at ambient temperature. Then 2.20 g (10.0 mmole) $P_4O_6$ was added slowly followed by 0.48 g (3.2 mmole) trifluoromethane sulfonic acid. The reaction mixture was heated to 80° C. for 1 hour. At ambient temperature 20 ml $H_2O$ was added; the obtained solution was evaporated to dryness and the solid was analysed by $^1$H- and $^{31}$P-NMR spectroscopy. 4-Morpholinyl-phenyl-methylphosphonic acid was detected at 72.9% w/w.

In table 2 examples 12 to 21, prepared according to the present invention are summarized. In this table the respective columns have the same meaning as the corresponding columns of table 1.

In table 2,
example 12 describes the synthesis of N-(hydroxymethyl) glycine methyl ester from reaction of glycine methyl ester and formaldehyde followed by the formation of N-(phosphonomethyl)glycine through reaction with tetraphosphorus hexaoxide.
example 13 describes the synthesis of N,N',N',N'',N'' hydroxymethyl-(2-aminoethyl)ethane-1,2-diamine followed by the formation of N,N',N',N'',N''-phosphonomethyl-(2-aminoethyl)ethane-1,2-diamine through reaction with tetraphosphorus hexaoxide.
example 14 to Example 17 describe the synthesis of N-hydroxymethyl-2,5-oxazolidinedione from reaction of 2,5-oxazolidinedione and formaldehyde followed by the formation of N-(phosphonomethyl)glycine through reaction with tetraphosphorus hexaoxide.
example 18 to 20 describe the synthesis of ethylenediamine-tetramethylenephosphonic acid from reaction of ethylenediamine, formaldehyde and tetraphosphorus hexaoxide in the presence of an acid catalyst wherein in example 18 and 20 formaldehyde and ethylenediamine are first reacted with the formation of N,N,N',N' tetrakis(hydroxymethyl) ethanediamine followed by the reaction with tetraphosphorus hexaoxide and wherein in
example 19 ethylenediamine and tetraphosphorus hexaoxide are first reacted followed by the addition of formaldehyde.
example 21 describes the synthesis of 4-morpholinyl-phenylmethanol from the reaction of morpholine and benzaldehyde, in the presence of an acid catalyst, followed by the formation of 4-morpholinyl-phenyl-methylphosphonic acid through the reaction with tetraphosphorus hexaoxide.

TABLE 1

| Ex | Aminoalkylol | OH (mole) | Solvent | Cata. (mole) | $P_4O_6$ (mole) | OH $P_4O_6$ | Cata OH | Cata $P_4O_6$ | $T_1$ ° C. | $T_2$/time ° C./hrs | $T_3$/time ° C./hrs | Yield (%) |
|---|---|---|---|---|---|---|---|---|---|---|---|---|
| 1 | N-hydroxymethyl acetamide | 40 | Trifluoromethanesulfonic acid Acetonitrile (10 ml) | 1 | 10 | 4.0 | 0.025 | 0.1 | 25 | 80/3 | 100/2 | 15.5 |
| 2 | N-hydroxymethyl phthalimide | 10 | Methanesulfonic acid | 130 | 2.5 | 4.0 | 13 | 52 | 60 | 85/16 | 80/1 | 11.5 |
| 3 | N-hydroxymethyl phthalimide | 40 | Trifluoromethanesulfonic acid 1,4-dioxane (10 ml) | 1 | 10 | 4.0 | 0.03 | 0.1 | 25 | 80/8 | 25/1 | 90.4 |
| 4 | N-hydroxymethyl-N'-phenyl hydantoin | 10 | Methanesulfonic acid | 108 | 2.7 | 3.7 | 10.8 | 40.0 | 40 | 40/16 | 40/1 | 18.5 |
| 5 | N-hydroxymethyl oxazolidinone | 15 | Methanesulfonic acid | 123 | 3.9 | 3.8 | 8.2 | 31.6 | 25 | 60/16 | 25/1 | 39.7 |

TABLE 1-continued

| Ex | Aminoalkylol | OH (mole) | Solvent | Cata. (mole) | P$_4$O$_6$ (mole) | OH P$_4$O$_6$ | Cata OH | Cata P$_4$O$_6$ | T$_1$ °C. | T$_2$/time °C./hrs | T$_3$/time °C./hrs | Yield (%) |
|---|---|---|---|---|---|---|---|---|---|---|---|---|
| 6 | N-hydroxymethyl pyrrolidinone | 30 | Methanesulfonic acid | 308 | 7.4 | 4.1 | 10.3 | 41.6 | 25 | 80/16 | 25/1 | 94.1 |
| 7 | N-hydroxymethyl pyrrolidinone | 20 | Trifluoromethanesulfonic acid | 170 | 4.9 | 4.1 | 8.5 | 34.7 | 25 | 80/16 | 25/1 | 73.0 |
| 8 | N-hydroxymethyl pyrrolidinone | 30 | Trifluoroacetic acid | 313 | 7.4 | 4.1 | 104 | 42.3 | 25 | 70/16 | 25/1 | 94.9 |
| 9 | N-hydroxymethyl pyrrolidinone | 30 | Trifluoromethanesulfonic acid 1,4-dioxane (25 ml) | 6 | 7.4 | 4.1 | 0.2 | 0.8 | 25 | 70/16 | 25/1 | 85.7 |
| 10 | N-hydroxymethyl pyrrolidinone | 30 | Trifluoromethanesulfonic acid acetonitrile (25 ml) | 6 | 7.4 | 4.1 | 0.2 | 0.8 | 25 | 70/16 | 25/1 | 96 |
| 11 | N,N'-bismethylol urea | 40 (80) | Methanesulfonic acid | 308 | 10 | 4.0 (8.0) | 7.7 | 30.8 | 70 | 80/4 | 150/8 | 34.8 |

TABLE 2

| Ex | Aminoalkylol | OH (mole) | Solvent | Cata. (mole) | P$_4$O$_6$ (mole) | OH P$_4$O$_6$ | Cata OH | Cata P$_4$O$_6$ | T$_1$ °C. | T$_2$/time °C./hrs | T$_3$/time °C./hrs | Yield (%) |
|---|---|---|---|---|---|---|---|---|---|---|---|---|
| 12 | N-hydroxymethyl glycine methylester | 1000 | Methanesulfonic acid | 18500 | 250 | 4.0 | 18.5 | 74 | 25 | 60/1 | 110/0.5 | 5.2 |
| 13 | Diethylenetriamine penta(hydroxymethylene) | 800 (4000) | Trifluoroacetic acid | 5000 | 250 | 3.2 (16) | 6.25 (1.25) | 20 | 35 | 60/0.33 | 85/0.25 | 10 |
| 14 | N-hydroxymethyl 2,5-oxazolidinedione | 9.9 | Trifluoroacetic acid | 104 | 2.5 | 4.0 | 10.5 | 41.6 | 50 | 50/24 | 50/72 | 42.5 |
| 15 | N-hydroxymethyl 2,5-oxazolidinedione | 9.9 | Trifluoroacetic acid | 104 | 2.5 | 4.0 | 10.5 | 41.6 | 50 | 50/24 | 50/72 | 44.7 |
| 16 | N-hydroxymethyl 2,5-oxazolidinedione | 9.9 | Trifluoroacetic acid | 104 | 2.5 | 4.0 | 10.5 | 41.6 | 25 | 60/24 | 60/8 | 34.9 |
| 17 | N-hydroxymethyl 2,5-oxazolidinedione | 9.9 | Methanesulfonic acid toluene (8 ml) | 15 | 2.5 | 4.0 | 1.5 | 6.0 | 80 | 60/5 | 60/8 | 5.6 |
| 18 | N,N,N'N' hydroxymethyl ethylenediamine | 61.5 (246) | Methanesulfonic acid | 985 | 61.6 | 1.0 (4.0) | 16.0 (4.0) | 16.0 | 50 | 85/1 | 25/1 | 36.6 |
| 19 | N,N,N'N' hydroxymethyl ethylenediamine | 184.4 (738) | Methanesulfonic acid | 985 | 184.7 | 1.0 (4.0) | 5.3 (1.3) | 5.3 | 70 | 105/1 | 25/1 | 57.5 |
| 20 | N,N,N'N' hydroxymethyl ethylenediamine | 61.5 (246) | Methanesulfonic acid | 985 | 61.6 | 1.0 (4.0) | 16.0 (4.0) | 16.0 | 55 | 80/3 | 25/1 | 31.9 |
| 21 | 4-morpholinyl-phenylmethanol | 40.0 | Trifluoromethane-sulfonic acid 1,4-dioxane (10 ml) | 4.0 | 10.0 | 4.0 | 0.1 | 0.4 | 25 | 80/1 | 25/1 | 72.9 |

The invention claimed is:

1. A method for the synthesis of an aminoalkylenephosphonic acid or its phosphonate esters, comprising the following steps:
a) forming, in the presence of an aldehyde or ketone and an acid catalyst, a reaction mixture by mixing a compound (a.1.) comprising at least one HNR$^1$R$^2$ moiety or a salt thereof, with a compound (a.2.) having one or more P—O—P anhydride moieties, said moieties comprising one P atom at the oxidation state (+III) and one P atom at the oxidation state (+III) or (+V), wherein the ratio of moles of aldehyde or ketone to N—H moieties is 1 or more and wherein the ratio of N—H moieties to P—O—P anhydride moieties is 0.3 or more,
and wherein:
the HNR$^1$R$^2$ moiety comprising compound (a.1.) is characterized in that:
R$^1$ and R$^2$ are independently selected from the group consisting of hydrogen, C$_1$-C$_6$ alkyl, C$_1$-C$_6$ alkenyl, C$_1$-C$_6$ acyl, optionally comprising one or more heteroatoms selected from the group consisting of oxygen, nitrogen and sulfur and optionally comprising one or more carbonyl moieties, wherein R$^1$ and R$^2$ may combine to form a 5-6 membered substituted or unsubstituted ring wherein N—H is incorporated in said ring, and wherein:
the compound (a.2.) comprising one or more P—O—P anhydride moieties, with said moieties comprising one P atom at the oxidation state (+III) and one P atom at the oxidation state (+III) or (+V), is selected from the group consisting of:
tetraphosphorus hexaoxide, P$_4$O$_7$, P$_4$O$_8$, P$_4$O$_9$, tetraethylpyrophosphite, and combinations thereof; and
b) recovering the resulting compound comprising aminoalkylene phosphonic acid or one of its phosponate esters.

2. The method according to claim 1, wherein the ratio of N—H moieties to P—O—P moieties is comprised between 0.3 and 2.0.

3. The method according to claim 1, wherein the reaction of step a) is performed at a temperature comprised between 20° C. and 120° C., for a period of time comprised between 30 minutes and 24 hours.

4. The method according to claim 1 comprising the additional steps of:
adding water to the reaction mixture after completion of the conversion of the HNR$^1$R$^2$ moiety comprising compound into the aminoalkylenephosphonic acid comprising compound;
bringing the reaction mixture comprising the added water, to a temperature comprised between 20° C. and 150° C. and
maintaining the reaction mixture comprising the added water at said temperature for at least 10 minutes.

5. The method according to claim 1, wherein the compound (a.2.) comprising the P—O—P anhydride moiety is selected from the group consisting of tetraphosphorus hexaoxide, and tetraethylpyrophosphite.

6. The method according to claim 1, wherein the compound (a.2.) comprising the P—O—P anhydride moieties is tetraphosphorus hexaoxide.

7. The method according to claim 1, wherein the aldehyde has the general formula R—CO—H and R is selected from the group consisting of hydrogen, aliphatic moiety, araliphatic moiety, aromatic moiety and heterocyclic moiety wherein the total number of carbon and hetero atoms is comprised between 1 and 11.

8. The method according to claim 1, wherein the ketone has the general formula R'—CO—R" and R' and R" are independently selected from the group consisting of aliphatic moiety, araliphatic moiety and aromatic hydrocarbon moiety wherein the total number of carbon atoms is comprised between 1 and 12.

9. The method according to claim 1, wherein the aldehyde is formaldehyde.

10. The method according to claim 1, wherein the acid catalyst is a homogeneous Brønsted acid catalyst selected from the group consisting of methanesulfonic acid, trifluoromethanesulfonic acid, trifluoroacetic acid, p-toluenesulfonic acid, hydrochloric acid, phosphorous acid, phosphoric acid and mixtures thereof.

11. The method according to claim 1, wherein the acid catalyst is a heterogeneous Brønsted acid selected from the group consisting of:
(i) solid acidic metal oxide combinations as such or supported by a carrier material;
(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;
(iii) organic sulfonic, carboxylic and phosphonic Brønsted acids which are substantially immiscible in the reaction medium at the reaction temperature;
(iv) an acid catalyst derived from:
the interaction of a solid support having a lone pair of electrons onto which is deposited an organic Brønsted acid;
the interaction of a solid support having a lone pair of electrons onto which is deposited a compound having a Lewis acid site; or
heterogeneous solids functionalized by chemical grafting with a Brønsted acid group or a precursor therefore; and
(v) heterogeneous heteropolyacids of the general formula $H_xPM_yO_z$ wherein P is selected from phosphorus and silicon and M is selected from tungsten and molybdenum and combinations thereof.

12. The method according to claim 1, wherein the acid catalyst is a homogeneous Lewis acid selected from the group consisting of $LiN(CF_3SO_2)_2$, $Mg(OCF_3SO_2)_2$, $Al(OCF_3SO_2)_3$, $Bi(OCF_3SO_2)_3$, and $Sc(OCF_3SO_2)_3$.

13. The method according to claim 1, wherein the acid catalyst is a heterogeneous Lewis acid obtained from the interaction of a homogeneous Lewis acid catalyst and an organic or inorganic polymer compound.

14. The method according to claim 1, wherein the reaction mixture of step a) comprises a solvent selected from the group consisting of 1,4-dioxane, toluene, ethylacetate, acetonitrile, acetic acid, sulfolane, 1-ethyl-3-methyl-imidazolium bis(trifluoromethylsulfonyl)imide, or a mixture thereof.

15. The method according to claim 1, which comprises the steps of:
a) forming a reaction mixture by mixing a compound (a.1.) comprising at least one $HNR^1R^2$ moiety with an aldehyde or a ketone and an acid catalyst optionally in the presence of a solvent, to form a compound comprising at least one aminoalkylol moiety;
b) adding a compound (a.2.) comprising at least one P—O—P anhydride moiety, having one P atom at the oxidation state (+III) and one P atom at the oxidation state (+III) or (+V) to the reaction mixture of step a) comprising at least one aminoalkylol moiety, to form a compound comprising aminoalkylenephosphonic acid;
c) adding water to the reaction mixture of step b); and
d) recovering the resulting compound comprising aminoalkylenephosphonic acid or one of its phosphonate esters.

16. The method according to claim 1, wherein the hydrolysis, after completion of the formation of the compound comprising aminoalkylenephosphonic acid, is performed at a pH comprised between 4.0 and 7.0.

17. The method according to claim 1, wherein the hydrolysis, after completion of the formation of the compound comprising aminoalkylenephosphonic acid, is performed at a temperature comprised between 20° C. and 150° C. for a period comprised between 10 minutes and 72 hours.

18. The method according to claim 1, wherein the ratio of N—H moieties to P—O—P moieties is comprised between 0.5 and 1.5.

19. The method according to claim 3, wherein the reaction of step a) is performed for a period of time comprised between 1 hour and 20 hours.

20. The method according to claim 1, wherein the reaction of step a) is performed at a temperature comprised between 40° C. and 100° C., for a period of time comprised between 30 minutes and 24 hours.

21. The method according to claim 20, wherein the reaction of step a) is performed for a period of time comprised between 1 hour and 20 hours.

22. The method according to claim 17, wherein the hydrolysis, after completion of the formation of the compound comprising aminoalkylenephosphonic acid, is performed for a period comprised between 1 hour and 10 hours.

23. The method according to claim 1, wherein the hydrolysis, after completion of the formation of the compound comprising aminoalkylenephosphonic acid, is performed at a temperature comprised between 40° C. and 100° C., for a period comprised between 10 minutes and 72 hours.

24. The method according to claim 23, wherein the hydrolysis, after completion of the formation of the compound comprising aminoalkylenephosphonic acid, is performed for a period comprised between 1 hour and 10 hours.

25. The method according to claim 1, wherein the compound (a.1.) comprising at least one $HNR^1R^2$ moiety or a salt thereof is selected from the group consisting of N,N'-bis(hydroxymethyl)ethylenediamine, N-hydroxymethylacetamide, N-(2-aminoethyl)ethane-1,2-diamine, N,N'-bismethylolurea, glycine methyl ester, N-hydroxymethyl glycine methyl ester, ethylenediamine, morpholine, 2,5-oxazolidinedione, and combinations thereof.

26. The method according to claim 1, wherein the compound (a.2.) comprising the P—O—P anhydride moiety is selected from the group consisting of tetraphosphorus hexaoxide, $P_4O_7$, $P_4O_8$, and $P_4O_9$.

* * * * *